US006215231B1

(12) United States Patent
Newnham et al.

(10) Patent No.: US 6,215,231 B1
(45) Date of Patent: Apr. 10, 2001

(54) HOLLOW SPHERE TRANSDUCERS

(75) Inventors: Robert E. Newnham, State College, PA (US); Joe K. Cochran, Marietta, GA (US); Sedat Alkoy, Akhisar (TR)

(73) Assignee: The Penn State Research Foundation, University Park, PA (US)

( * ) Notice: Subject to any disclaimer, the term of this patent is extended or adjusted under 35 U.S.C. 154(b) by 0 days.

(21) Appl. No.: 09/304,911

(22) Filed: May 4, 1999

Related U.S. Application Data

(60) Provisional application No. 60/084,059, filed on May 4, 1998, and provisional application No. 60/103,070, filed on Oct. 5, 1998.

(51) Int. Cl.⁷ .................................................. H01L 41/08
(52) U.S. Cl. ......................... 310/371; 310/311; 310/340
(58) Field of Search ................................... 310/311, 340, 310/371

(56) References Cited

U.S. PATENT DOCUMENTS

| | | | |
|---|---|---|---|
| 2,565,158 | * | 8/1951 | Williams .............................. 310/371 |
| 2,565,159 | * | 8/1951 | Williams .............................. 310/371 |
| 2,645,727 | * | 7/1953 | Willard ................................ 310/371 |
| 2,939,970 | * | 6/1960 | Dranetz et al. ...................... 310/371 |
| 3,150,592 | * | 9/1964 | Stec ..................................... 310/371 |
| 3,230,504 | * | 1/1966 | Horan et al. ........................ 310/371 |
| 3,317,762 | * | 5/1967 | Corwin et al. ...................... 310/334 |
| 3,891,871 | * | 6/1975 | Henriquez et al. ................. 310/371 |
| 4,184,094 | * | 1/1980 | Kopel .................................. 310/335 |
| 4,276,491 | * | 6/1981 | Daniel ................................. 310/317 |
| 4,618,796 | * | 10/1986 | Riedlinger ......................... 310/311 |
| 4,777,154 | | 10/1988 | Torobin ................................ 501/84 |

OTHER PUBLICATIONS

"A System for Ultrasonic Beacon–Guidance of Catheters and Other Minimally–Invasive Medical Devices," by David Vilkomerson, *IEEE Transactions on Ultrasonics, Ferroelectrics, and Frequency Control*, vol. 44, No. 1, Jan. 1997.

* cited by examiner

Primary Examiner—Thomas M. Dougherty
(74) Attorney, Agent, or Firm—Thomas J. Monahan

(57) ABSTRACT

An electroactive device incorporating the invention is configured from an electroactive ceramic hollow sphere having an inner surface, an outer surface, a wall thickness aspect and a radius aspect. Conductive electrodes are positioned on opposed surfaces of said sphere and conductors enable application of an electrical potential between the conductive electrodes to enable a field to be applied to said sphere that causes a dimension change in the radius aspect and thickness aspect thereof. In one embodiment the sphere has a $d_{33}$ direction parallel to the thickness aspect, and $d_{31}$ & $d_{32}$ directions parallel to the sphere surfaces and in another embodiment the $d_{33}$ direction is perpendicular to the thickness aspect, and $d_{31}$ & $d_{32}$ directions are respectively parallel and perpendicular to the sphere surfaces. The sphere is preferably supported by a rod that either passes throng one opening in the sphere or through two opposed openings. Further, the rod may include a pathway for other instrumentality's. Arrays of such devices are also disclosed.

26 Claims, 11 Drawing Sheets

(A) XY PLANE-50 kHz   (B) XY PLANE-100 kHz

HOLLOW SPHERE TRANSDUCERS

This application claims benefit to U.S. provisional application Serial No. 60/084,059, filed May 4, 1998 and application Serial No. 60/103,070 filed Oct. 5, 1998.

This invention was made with Government support under Grant N00014-98-1-0222 awarded by the Office of Naval Research. The Government has certain rights in the invention.

FIELD OF INVENTION

This invention relates to electroactive ceramic transducers (piezoelectric, electrostrictive, etc.) and, more particularly to sensors/actuators that are based on a hollow sphere shape, and their composites with polymers.

BACKGROUND OF THE INVENTION

Every year more than one million balloon angioplasty procedures are performed in the United States. These medical procedures are carried out in the abdominal cavity and in the arteries, using catheters and miniature ultrasonic instrumentation. Most of these interventional techniques use X-ray guidance, which requires expensive, non-mobile facilities, and use expensive and sometimes harmful "contrast" materials that produce only a projection image.

In contrast to the X-ray techniques, ultrasound guidance can be simpler and less expensive. It does not require a contrast media and provides three-dimensional information about the tissue structure. However, ultrasound guidance has not been used, until recently, because it requires visualization of a particular point on the catheter. The catheter itself has a high ultrasound reflectivity and visualization of it depends on the angle of the incident ultrasound beam. In order to solve this problem and make the appearance of a point on the catheter both independent of the angle and of the surrounding tissue reflectivity, Vilkomersan and co-workers (D. Vilkomersan et al., "Quasi-omnidirectional transducers for ultrasonic electronic-beacon guidance of invasive devices", *SPIE*, Vol. 1733, p.154–165, 1992) proposed a quasi-omnidirectional annular shaped ultrasonic sensor located on the catheter. Due to the difficulties in fabricating such a transducer from ceramic piezoelectrics, Vilkomersan et al. used a PVF2 copolymer as the ultrasonic sensor. However, it is known to those skilled in the art that polymer based piezoelectrics are associated with high dielectric losses and low electromechanical coupling coefficients and low dielectric constant.

An electroactive ceramic with low losses and high electromechanical coupling coefficients and high dielectric constant would be more suitable for the ultrasonic guidance of a catheter. However, machining a quasi-omnidirectional annular shaped ultrasonic sensor from a fragile ceramic, with current techniques, is not feasible. Also to be considered are the health concerns and hygienic requirements associated with catheters.

Catheters are discarded after one use to prevent spreading of blood-borne diseases. Considering the high volume of use of these interventional techniques, there is need for small, inexpensive transducers for use in assisting the guidance of catheters.

In clinical applications of ultrasonic transducers, such as Ultrasonic Backscatter Microscopy and Ultrasonic Imaging Catheters, higher axial and lateral resolution requires operating frequencies greater than 20 MHz. In recent years transducers operating in this range have been prepared from piezoelectric polymers as well as from piezoelectric ceramics. See: M. S. Shearer et al., "The design and fabrication of high frequency poly (vinylidene fluoride) transducers," *Ultrasonic Imaging*, vol. 11, pp. 75–94, 1989, and F. S. Foster et al., "Characterization of lead zirconate titanate ceramics for use in miniature high-frequency (20–80 MHz) Transducers," *IEEE Trans. Ultrason. Ferroelec. Freq. Contr.*, vol. 38, no.5, pp. 446–453, 1991.

Polymer-based transducers have good beam properties, broad bandwidth, and can be fabricated easily into various shapes, but as stated above, they are also associated with high losses and low electromechanical coupling coefficients. Ceramic transducers, with their high coupling coefficients and low losses, lead to improved image qualities.

However, obtaining a high resolution image requires a focused ultrasound beam. Using an electronically steerable array of transducers to obtain a focused beam is not feasible due to size limitations imposed on the transducer at an operating frequency of >20 MHz. Also electronic steering requires extensive use of expensive electronic equipment. Therefore, the easiest way to obtain a focused ultrasound beam requires a spherically shaped transducer. However, molding, or machining a focused transducer (wall thickness <100 $\mu$m due to the operating frequencies) using conventional techniques is not feasible. See: Lockwood et al. "Fabrication of high frequency spherically shaped ceramic transducers," *IEEE Trans. Ultrason. Ferroelec. Freq. Contr.*, vol. 41, no. 2, pp. 231–235, 1994. Lockwood et al. developed a bending technique to obtain a spherical shape from very thin ceramic plates. A ceramic plate was bonded to a malleable material, such as an epoxy. This layered composite structure was shaped into a shallow spherical shell by gently pressing it against a ball bearing at 65° C.

While this approach worked fairly well for high f-number transducers at very high frequencies (f-number=focal length/aperture size), it is difficult to apply the technique for transducers that operate below 40 MHz, and that have a lower f-number, where the ceramic thickness hinders the bending process. Moreover, Zipparo et al., ("Piezoceramics for high-frequency (20 to 100 MHz) single-element imaging transducers," *IEEE Trans. Ultrason. Ferroelec. Freq. Contr.*, vol. 44, no. 5, pp. 1038–1048, 1997) reported a decrease in electromechanical coupling, dielectric constant, mechanical compliance, and an increase in mechanical losses of the ceramic, along with microcracks, resulting from this bending process.

In addition to the biomedical area, miniature ultrasonic probes have also been used for mapping the field of a hydrophone as well as the non-acoustic field of turbulent flow. There are several important requirements for microprobe sensors in these applications. In detecting underwater signals, omnidirectionality is highly advantageous. Additionally smaller sizes are necessary in some applications. Accurate mapping of an acoustic field requires that: (i) the physical dimensions of the probe should be smaller than the acoustical wavelength of interest (i.e. with a size in the millimeter range), (ii) the resonance frequencies of the probe should be well above the frequency range of interest (usually <200 kHz), (iii) they should exhibit adequate sensitivity with an acceptable signal-to-noise ratio and a wide bandwidth.

Although, volume expanders with spherical shape are thought to be the best way to achieve omnidirectionality, again there are problems associated with fabricating spherical transducers with sizes in the millimeter range. There are hollow sphere shaped transducers available, commercially produced by machining and grinding hemispheres from bulk ceramics using conventional techniques. These hemispheres are then attached together using an adhesive agent. However, the machining from bulk is a laborious and expensive process. Most importantly there are limitations on the smallest size and the radius to thickness ratio, r/t, achievable through these techniques. This r/t ratio becomes important in the operation of the hollow sphere transducer and can be dubbed as the amplification factor in the calculation of figure of merit of a hollow sphere hydrophone.

Based on the above, there is a need for transducers with omnidirectional receive and transmit sensitivity, small sizes (<1 cm for underwater applications and <2 mm for ultrasound guidance applications) and high sensitivities. There also is a need for focused transducers that operates at high frequencies (>20 MHz).

Millimeter size thin-walled hollow sphere transducers made of piezoelectric material, PZT-5 (lead zirconate titanate), were first fabricated at our laboratories several years ago (See: R. Meyer Jr. et al., "PZT hollow sphere transducers", *J. Amer. Ceram. Soc.*, vol. 77, 6, pp. 1669–72, 1994). Green (un-fired) spheres were produced using a coaxial nozzle slurry process. The process was based on the U.S. Pat. No. 4,671,909 to Torobin and further developed in the Materials Science and Engineering Department of the Georgia Institute of Technology to mass produce ceramic and metallic hollow spheres (See A. T. Chapman et al., "Thin-wall hollow spheres from slurries", DOE-ECUT Program, ONRL Subcontract 86X-22043C, *Annual Reports*, 1987, 1988, 1989). Fabrication of green hollow spheres included preparation of a slurry of a fine-grained powder of the electroactive ceramic material (piezoelectric, electrostrictive, etc.) along with appropriate binders and dispersants (such as, but not limited to, poly methylmethacrylate (PMMA), polyvinyl alcohol (PVA)) and acetone. This slurry was then injected through a coaxial nozzle with air passing through the center tube. The slurry formed a hollow cylindrical form as it left the nozzle. The bottom of the cylinder later closed with surface tension, and air pressure created a bubble.

At a certain inner pressure the bubble breaks free from the rest of the slurry, closing the upper end and forming a hollow sphere. This process has been shown to be a flexible technique for the fabrication of high volume of hollow spheres of different ceramic compositions, with fairly uniform diameters from 1 to 6 mm, and wall thicknesses ranging from 12 to 150 μm. These green spheres are subsequently fired for binder burnout, and sintered at high temperature. Due to their similarity to ball bearings and to the spherical pellets used in air rifles in shape and size, electroactive ceramic hollow spheres are called "BBs" or "BB transducers".

In the prior art, sintered electroactive ceramic hollow spheres 10 were poled radially, as shown in FIG. 1 hereof, utilizing an inner electrode access hole 12, a conductive inner electrode 14 and a conductive outer electrode 16, or poled tangentially, shown in FIG. 2, utilizing external conductive electrodes located on the top 18 and bottom 20 parts of the sphere. Wire electrode leads 22 are attached to the spheres using a conductive epoxy adhesive 24.

When a potential is applied across electrodes 14 and 16, in the radial poling case, the ceramic sphere expands and shrinks volumetrically ($d_{31}$ breathing vibration mode and $d_{33}$ wall thickness vibration mode).

In the case of tangentially poled spheres, when a potential is applied across electrodes 14 and 16, the ceramic sphere deforms mainly in an elliptical fashion utilizing $d_{31}$ & $d_{33}$.

While a substantially sensitive sensor is thus obtained, there are problems associated with this design. Namely, the wires used as electrical leads do not provide a solid and compact transducer design. As a result, when used in underwater applications, the transducers tend to wobble or shift from their position in three-dimensional space. Second, a problem associated with especially the radially poled design is the epoxy adhesive used in the outer electrode wire attachment. This epoxy creates an asymmetrical mass loading on the transducer and disturbs the omnidirectional receive and transmit properties. The third problem is the acoustic impedance ($Z_a$) mismatch between the ceramic material ($Z_a \approx 30$ MRayl) and the fluid medium ($Z_a \approx 1.5$ Mrayl) in which it will be used.

Accordingly, it is an object of this invention to provide electroactive ceramic hollow sphere transducers with omnidirectional receive and transmit response, with small size (<1 cm for underwater applications and <2 mm for ultrasound guidance applications).

It is another object of this invention to provide focused transducers with low f-numbers that can operate at frequencies higher than 20 MHz.

It is also an object of this invention to provide arrays and polymer-electroactive ceramic composites of these hollow sphere transducers for underwater sensing and non-destructive testing applications.

It is a further object of this invention to provide an inexpensive fabrication technique that will allow production of throwaway spherically shaped electroactive ceramic transducers.

SUMMARY OF THE INVENTION

An electroactive device incorporating the invention is configured from an electroactive ceramic hollow sphere having an inner surface, an outer surface, a wall thickness aspect and a radius aspect. Conductive electrodes are positioned on opposed surfaces of said sphere and conductors enable application of an electrical potential between the conductive electrodes to enable a field to be applied to said sphere that causes a dimension change in the radius aspect and thickness aspect thereof. In one embodiment the sphere has a $d_{33}$ direction parallel to the thickness aspect, and $d_{31}$ & $d_{32}$ directions parallel to the sphere surfaces and in another embodiment the $d_{33}$ direction is perpendicular to the thickness aspect, and $d_{31}$ & $d_{32}$ directions are respectively parallel and perpendicular to the sphere surfaces. The sphere is preferably supported by a rod that either passes through one opening in the sphere or through two opposed openings. Further, the rod may include a pathway for other instrumentality's.

DETAILED DESCRIPTION OF THE INVENTION

Figure 3:
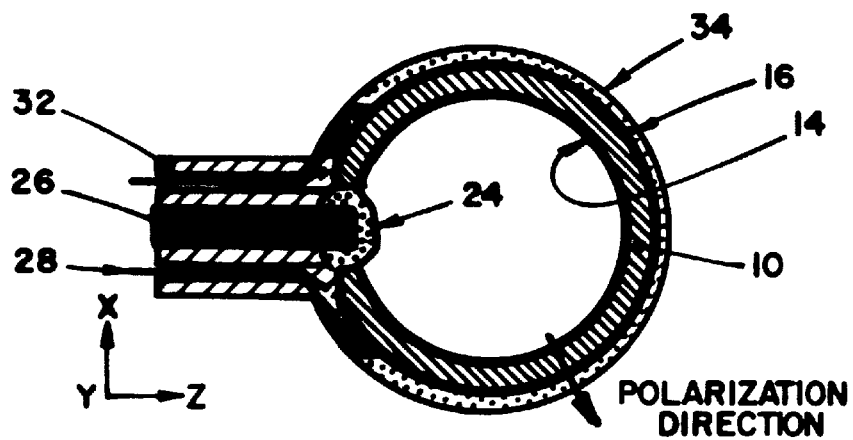
FIG. 3 is a side sectional view of a radially poled electroactive ceramic hollow sphere embodying the invention.

It has been determined that the deficiencies of the prior art structure shown in FIG. 1 can be overcome by our new design, as explained below. As shown in FIG. 3, to provide stability to radially poled spheres, a stiff rod, or needle-shaped material, or an inner core wire of a coaxial cable 26, preferably but not limited to metal, is used as the inner electrode connection attached to the inner electrode by a conductive adhesive 24 material. The outer electrode connection to the radially poled sphere is also changed and, instead of using a single wire and creating an asymmetric structure, a thin-walled conductive tube or a tube shaped braided wire frame of the outer wire layer of a coaxial cable 28 is used. This outer electrode lead is connected to outer electrode 16 by applying a thin ring-shape layer of conductive material 28, such as a silver paint or silver epoxy, around the rim of insulation gap 30.

Both inner electrode lead 26 and outer electrode lead 28 are covered with an electrical insulation layer 32. The outer surface of sphere 10, including the outer electrical connections are coated with a polymer layer 34 with a thickness adjusted for acoustic impedance matching. This coating can be applied by dipping the transducer into the polymer mix, by spray coating, by painting, or by depositing the layer.

Polymer layer 34 also acts as an electrical insulation layer between the transducer and the outer fluid medium, as well as a water-tight environmental insulation layer on the device. One example material is polyurethane, though it is not to be taken as a limitation on our invention, and other polymer materials can also be used. This polymer coating increases the mechanical strength of the sphere under hydrostatic pressure.

A further modification to this design is to use an electroactive polymer coating. An example of such a coating is a copolymer of piezoelectric polyvinylidene fluoride (PVDF) with trifluoroethylene (TrFE) or tetrafluoroethylene (TeFE), however, other electroactive (piezoelectric, electrostrictive) polymers can be used as well. Applying a conductive electrode layer on the outer surface of this electroactive polymer layer and poling it, or applying a bias electric field creates a second electromechanically active layer on the electroactive ceramic sphere (in addition to the advantages it provides in terms of acoustic matching and mechanical strength).

When a voltage is applied across the electrodes 14 and 16, or when an acoustic pressure is applied, the radially poled hollow sphere transducer displays omnidirectional receive and transmit responses due to the symmetry of the design. The maximum achievable radius to thickness ratio (r/t), or the so-called amplification factor, with these hollow spheres is around 50, which results in a two to three order of magnitude higher hydrophone figure of merit ($\sim 300 \times 10^{-12}$ $m^2/N$) compared to a bulk PZT ($60 \times 10^{-15}$ $m^2/N$).

The resonance frequency of the fundamental breathing mode of the hollow sphere depends on the radius of the sphere as well as the materials used in the transducer. However, for illustrative purposes and without limiting the invention, a frequency range of 400 kHz to 1.2 MHz can be given for PZT-5A (lead zirconate titanate) based hollow sphere transducers with radii from 1 to 2.5 mm. These are well above the frequency range of interest for an underwater ultrasound microprobe application. A detailed illustrative example of this embodiment of the invention is described in Example 1 below, along with experimental results.

Figure 4:
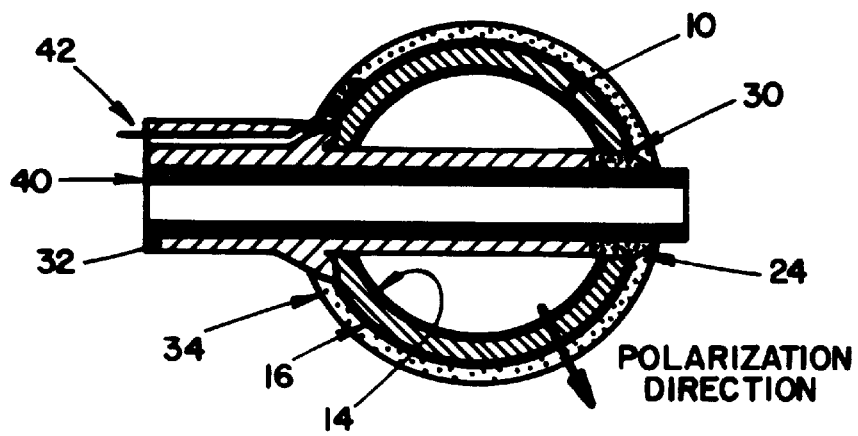
FIG 4 is a side sectional view of a radially poled quasi-omnidirectional electroactive ceramic hollow sphere embodying the invention.
Figure 5:
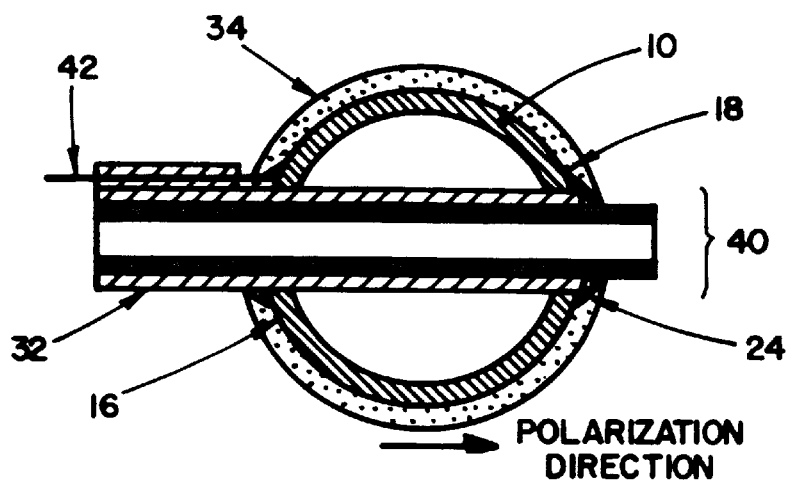
FIG. 5 is a side sectional view of a tangentially poled quasi-omnidirectional electroactive ceramic hollow sphere embodying the invention.

Another embodiment of our invention is a quasi-omnidirectional hollow sphere transducer shown in FIGS. 4 and 5. In these designs, two access holes 36 and 38 are opened on the opposite poles of the electroactive ceramic hollow spheres 10, creating an annular ring shaped, or a barrel shaped transducer which has quasi-omnidirectional receive and transmit characteristics. By having the center of these two access holes on the same axes it is possible to pass a cylindrically shaped core 40 such as, but not limited to, a rod, or a wire, or a needle of any conductive material, preferably a metal, through the sphere.

In the embodiment of the invention illustrated in FIGS. 4 and 5, this cylindrical core piece is drawn as a hollow cylindrical metal needle, which also acts as one of the electrical leads to the transducer. One possible use of this quasi-omnidirectional transducer is as a guidance beacon on a catheter where the cylindrical core piece can be the catheter itself. Having a hollow cylindrical core piece 40 allows further access through the sphere for things such as an optical fiber, or electrical connections for another transducer (i.e., used for imaging, or connections for a surgical piece, or the catheter).

In this embodiment of the invention, the core piece 40 is coated with an electrical insulation layer 32 and is connected either to inner electrode 14, in the case of a radially poled hollow sphere transducer, or to one of external electrodes 18, in the case of a tangentially poled hollow sphere. Second electrode lead 42 is illustrated in FIG. 4 and FIG. 5 as a conductive wire coated with an insulation layer 32. However, this is, again, one embodiment and is by no means intended to be limiting to the design of the device. The outer electrode lead design shown in FIG. 3, i.e., a thin-walled conductive tube 28 or a tube shaped braided wire frame, is applicable in this embodiment as well.

The entire device is again coated with a thin polymer layer 34 for similar reasons discussed for the embodiment presented in FIG. 3. The polymer that is to be used is selected based on the application intended for the transducer. An electrically passive polymer will provide electrical insulation and will be a water-tight coating, whereas an electroactive polymer can provide additional sensing characteristics. In the case of medical catheter applications the polymer has to provide a biologically inert coating, and has to be a medically approved polymer such as Parylene®. An illustrative example of this embodiment is described in Example 2, along with experimental results.

Figure 6:
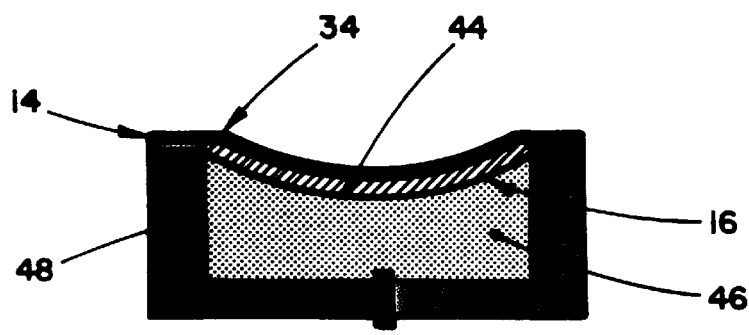
FIG. 6 is a side sectional view of a focused transducer devised from electroactive ceramic hollow spheres embodying the invention.

FIG. 6 illustrates another embodiment of the invention, using a hemisphere or preferably less than a hemisphere section 44 of an electroactive ceramic hollow sphere to obtain a focused ultrasound beam. Shell-shaped sphere sections are obtained by means of grinding, lapping, or cutting a full sphere. Both surfaces of concave shape 44 are coated with a conductive electrode material 14 and 16 by means of sputtering, painting, or such coating techniques.

This concave self-focused transducer may then be poled radially through its wall thickness. A conductive backing material 46 is then applied to the convex surface of the shell. The focused BB transducer is then mounted in a connector using a non-conductive polymer based filler 48. The concave surface of the transducer is then coated with a uniform, thin layer of an acoustic matching material. (See: S. Alkoy et al., "Focused Spherical Transducers for Ultrasonic Imaging", *Proceedings of the IEEE International Ultrasonics Symposium*, pp 991–996, 1997).

Compared to Lockwood's technique, the advantage of beginning from a full sphere and grinding it down to a shell is the ability to fabricate focused transducers with a wide range of f-numbers beginning from f=1. Additionally, since an extensive mechanical stress is not applied on the electroactive ceramic at any point in the fabrication process. Thus, the resultant transducers contain minimal or no damage in the form of microcracks that may adversely affect the final characteristics. An illustrative example of this embodiment of the invention is described in Example 3 below, accompanied with experimental results.

In addition to single element full sphere, or single element focused hemisphere transducers, arrays of BB transducers, examples of which are illustrated in FIG. 7, FIG. 8, FIG. 9 and FIG. 10 are also presented herein. Such arrays achieve higher transmit voltage responses and sensitivities, with directional receive and transmit characteristics. In the array fabrication, spheres are coated with conductive electrodes and are poled radially, or tangentially similar to their single element full sphere counter-parts explained above.

In this embodiment (see FIGS. 7–10), these elements are then mounted on a substrate 50 in an orderly fashion such as four spheres in a 2×2 array, or nine spheres in a 3×3 array, etc. using an adhesive material 52. Tiny via holes 54 may be drilled in the substrate, prior to mounting the spheres, to allow wire connections 22 to pass through. Spheres in these arrays are then connected electrically either in series, or in parallel. Radially and tangentially-poled spheres are both used in the arrays. These arrays of spheres are then coated with a thin layer of polymer 34 for the same reasons explained above, or embedded fully in a polymer matrix.

The designs given in FIGS. 7–10 are not the only possible configurations, and they are given merely as illustrative examples of the embodiment of the invention into arrays of electroactive ceramic hollow spheres containing more than one sphere element. Also included in this embodiment are flat, or curved, or conformable arrays of full spheres, arrays of spheres with various sizes of holes, arrays of hemispheres and arrays of less-than-hemisphere shell sections of spheres. More detailed description on the fabrication of these arrays along with experimental results are presented in the Example 4 below.

Figure 11:
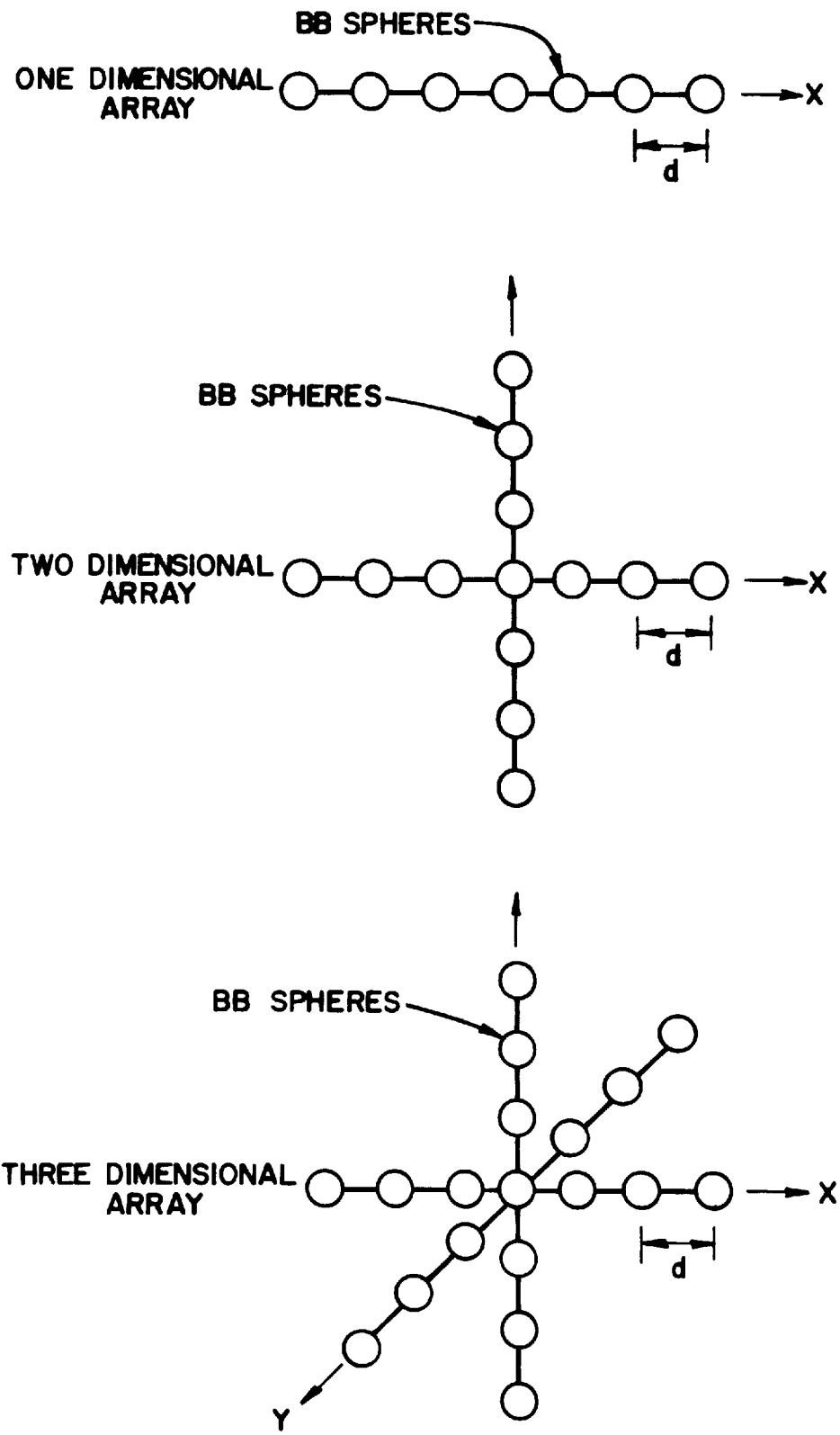
FIG. 11 is three different types (one dimensional, two dimensional and three dimensional) of line array of electroactive ceramic hollow spheres embodying the invention

Another embodiment (FIG. 11) of the invention is an underwater direction finder. Modified from the array designs discussed above, this device is prepared from one, two or three dimensional line array of electroactive ceramic hollow spheres. A major difference from the previous array designs is that all spheres in this device are not connected to each other electrically in series or in parallel. Instead each sphere or groups of spheres, separated from each other by an equal distance "d", are connected to their own, individual electronic circuitry.

The basic principle of this line array direction finder is as follows. When an acoustic wave originates from an arbitrary point in 3 D space with an arbitrary propagation direction, and reaches the line array of spheres, each sphere will detect the wavefront and the associated pressure change, at a different time due to their equidistant, separate locations in space. Combining the signals received by each sphere, with phase delays, will allow the direction of the acoustic wavefront and the source to be detected. Aside from the unique hydrophone properties of BBs; the advantage of using electroactive ceramic hollow spheres (BBs) over any other shape and design of transducer is the fact that BB spheres have omnidirectional receive and transmit response in three dimensions, up to very high frequencies. The upper frequency limit is the fundamental resonance frequency of the electroactive sphere, which is controlled by the dimensions of the sphere and the material properties of the ceramic. Therefore, a line array of BB spheres does not necessarily have to be fixed on a flat substrate, but instead they can be fixed on wire meshes, or used as towed arrays.

Figure 12:
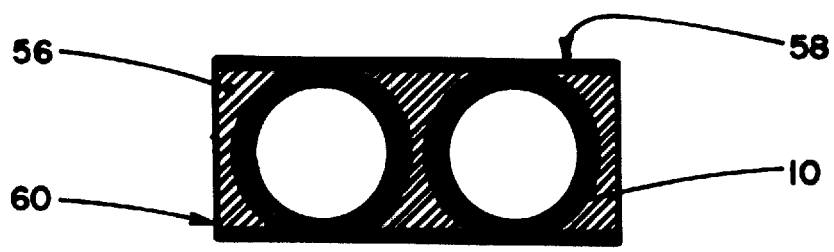
FIG. 12 is a side sectional view of electroactive ceramic hollow spheres—polymer composites with 0–3, or 1–3 connectivity embodying the invention.
Figure 13:
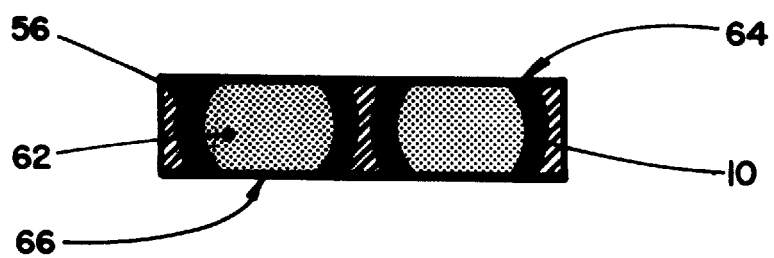
FIG. 13 is a side sectional view of electroactive ceramic hollow spheres—polymer composites with 1–3 connectivity embodying the invention.

FIGS. 12 and 13 illustrate another embodiment of the invention, with electroactive ceramic hollow spheres forming a composite structure within a polymer matrix. The design of FIG. 12 may have a 0–3 or 1–3 connectivity based on the location of the electrodes. The design in FIG. 13 is an example of a 1–3 connectivity. In this connectivity terminology (first proposed by Newnham et al in "Connectivity and piezoelectric-pyroelectric composites", *Mat. Res. Bull.*, vol. 13, p. 525–36, 1978), the first number corresponds to the self-connectivity of the active phase, in this case the electroactive ceramic hollow spheres, and the second number corresponds to the self-connectivity of the passive, matrix phase, such as a polymer filler.

Composites of BBs illustrated in FIG. 12 are prepared by arranging the spheres 10 into arrays in a mold and then pouring the polymer matrix 56 into the mold. After curing the polymer matrix and prior to poling, two parallel surfaces of the composites are coated with conductive electrodes 58 and 60 by either sputtering, spraying, or painting. If the poles of the spheres have contact with top 58 and bottom 60 electrode layers then the structure can be classified as having a 1–3 connectivity. If the spheres are fully embedded in the polymer matrix, and do not have any contact with the electrode layers, then the structure can be classified as having a 0–3 connectivity.

In the case of 1–3 composites, illustrated in FIG. 13, the composite structure is prepared in the same way with those in FIG. 12 and then the composite structure is ground down until the top and bottom polar cap sections of the spheres 10 are removed and the inner volume is exposed. This step is followed by filling this newly exposed empty inner volume with the same polymer used in the matrix. Finally, the composite is polished to a fine surface, and then both sides are coated with conductive electrodes and poled across the thickness dimension. Another way to prepare 1–3 composite avoids filling in the empty inner volumes 62. Instead, the two planar surfaces of the composite are coated with conductive electrodes and then thin caps (such as thin metal sheets) 64 and 66 are attached to the surfaces using an adhesive material.

The empty space and air trapped inside the BBs in the designs illustrated in FIG. 12 and FIG. 13 provides an opportunity to produce very low density composite hydrophones which have a good acoustic impedance match with water. Due to the very small wall thickness that can be achieved with the BBs, the 1–3 design illustrated in FIG. 13 allows a very low ceramic content in the composite.

The designs presented in FIG. 12 and FIG. 13 are two embodiments of composite forms of the invention. However, these two are not to be interpreted as limiting, and the invention may be embodied in various forms to form composites of electroactive ceramic hollow spheres with a second phase matrix material (e.g., polymers) as well as other materials that are not specifically mentioned here.

The following examples illustrate the preparation of electroactive hollow sphere transducers in various embodiments in accordance with the invention.

EXAMPLE 1

Figure 1:
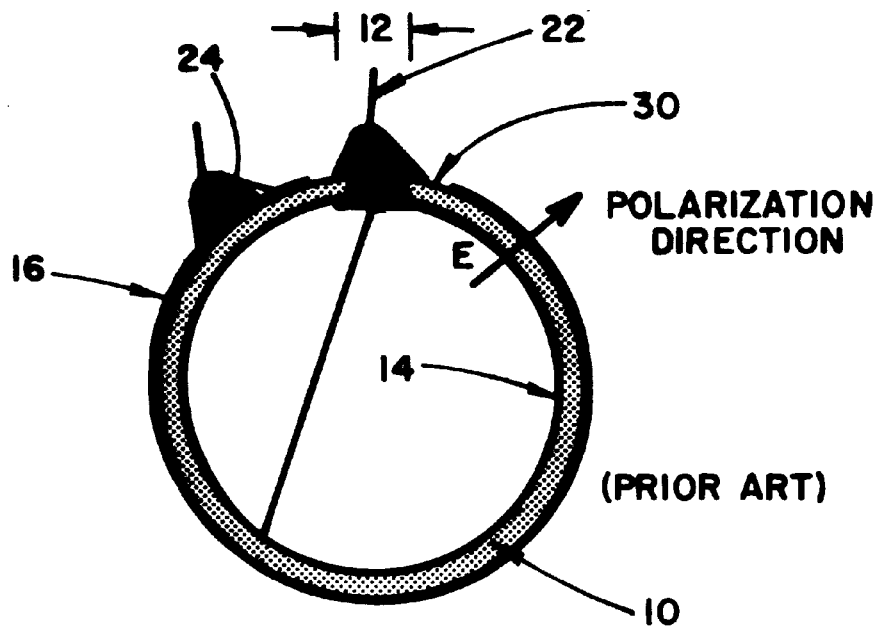
FIG. 1 is a side sectional view of a radially poled hollow sphere transducer from the prior art.
Figure 2:
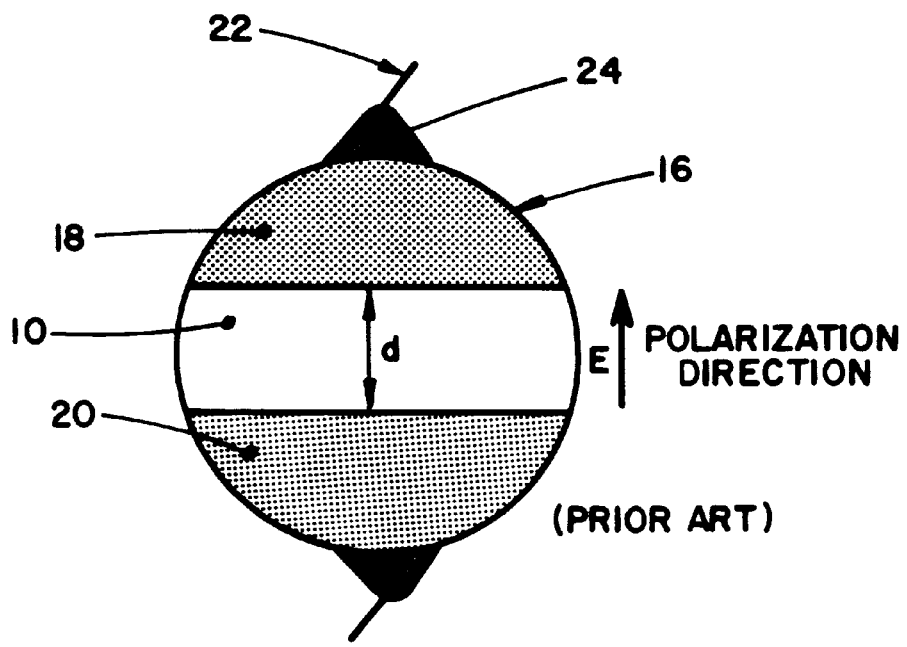
FIG. 2 is a side view of a tangentially poled hollow sphere transducer from the prior art.

In the prior art transducer shown in FIG. 1 (See: S. Alkoy et al., *IEEE Trans. Ultrason., Ferroelect., Freq. Contr.*, 44, 5, pp 1067–1076 (1997), a fired-on silver electrode (Conductor Composition 7095, DuPont), or an air-dry silver paint (Conductive Silver 200, Demetron GmbH) was applied to the inner surface of the spheres by injecting the liquid electrode through an electrode access hole with a ~450 $\mu$m diameter. This was followed either by a firing step at 600° C. for 30 minutes for fired-on electrode, or a drying step at 80° C. for 30 minutes for an air-dry electrode. Silver electrical lead wires were attached and the electrode hole was sealed using a conductive silver epoxy adhesive (E-solder #3021 from Insulating Materials, Inc.). A thin layer of gold was deposited as the external electrode.

While, a reasonably sensitive sensor was obtained in the previous work, there were problems associated with the design. Most important of these were problems associated with the inner electrode. It was not feasible to control the thickness and uniformity of the inner electrode with the injection technique used. In some cases the silver inner electrode layer was found to have a thickness comparable to the ceramic sphere wall thickness. In the case of a fired-on silver electrode, the electrode layer was found to shrink during the firing process at 600° C. and lose its contact with the inside surface of the sphere.

These two problems are thought to result in damped vibrations and incomplete poling, yielding transducers with low capacitance. In an effort to solve these problems improvements were made in the fabrication of the transducers.

Following the sintering step, spheres are encased in Crystal Bond™. Then the encased spheres are ground down on one side to open the inner electrode access hole with a diameter of ≧1.0 mm. This large hole allowed us to coat the inner surface of the sphere with a silver electrode through an evaporation-deposition technique. The outer surface of the spheres is electroded with silver, again using the evaporation-deposition technique. Uniform inner and outer electrode layers were obtained. The electroactive spheres were then poled radially in a silicone oil bath at 120° C. by applying an electric field of 50 kV/cm for 10 minutes.

As a result of the uniform electrode layers obtained in this process, improved dielectric and piezoelectric properties were observed with increased capacitance (4000 to 5000 pF for spheres with 1.38 mm radius, ~90 $\mu$m wall thickness and 1.8 mm hole diameter) and higher admittance values. A clean admittance vs. frequency response was obtained, a sign of an active, well poled ceramic, free of clamping. Poled spheres were then cleaned from the residue silicone oil using acetone, or alcohol, and dried in air.

In addition to the inner electrode problems, the prior art shown in FIG. 1 required a new design in order to be used as a hydrophone. Since the electrode wires did not provide a solid frame to hold the hydrophone in a fixed position underwater, they were replaced by a coaxial electrical cable that also provides protection from EM interference. The inner core wire of the coaxial cable was attached to the inner electrode of the sphere using silver epoxy adhesive (E-solder #3021 from Insulating Materials, Inc.). After 24 hours in-air, room temperature drying period the inner electrode wire and its connections were coated with an insulating epoxy adhesive (3 parts 45LV Eccobond epoxy resin and one part 15LV hardener from Emerson and Cuming, Inc.) for electrical insulation between the inner and outer electrodes. Another 24 hours was given for the insulating epoxy to cure.

The outside electrode connection design with a silver epoxy contact was also replaced. In the prior art, this silver epoxy adhesive created an asymmetrical mass loading on the transducer, and therefore, disturbed the omnidirectional receive and transmit characteristics. By using a circumferential contact around the electrode hole, this mass loading is distributed evenly in the present hydrophone design. The electrical connection between the outer braided wire of the coaxial cable and the outer electrode of spheres was provided using air-dry silver paint (Conductive Silver 200 from Demetron GmbH).

Figure 14:
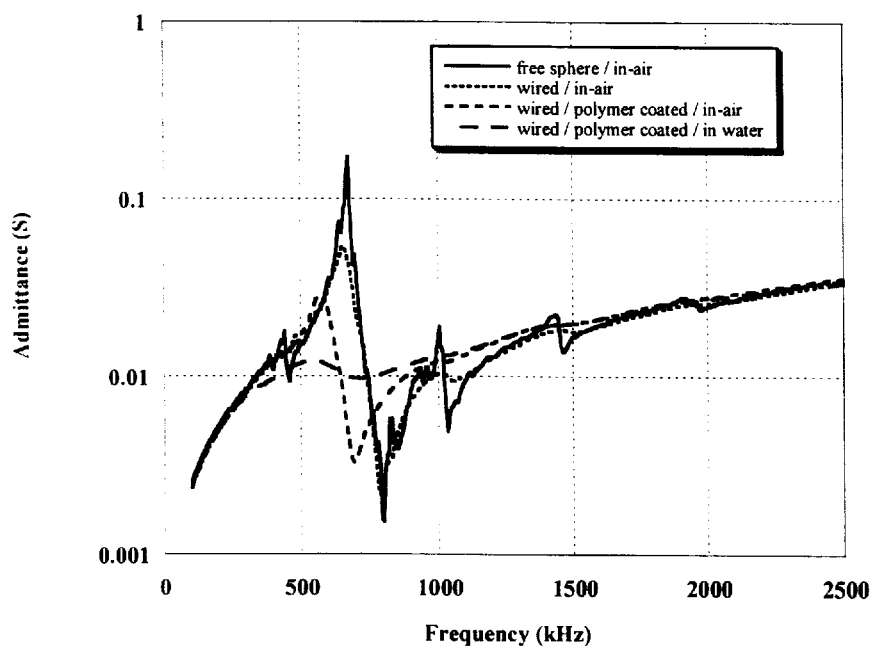
FIG. 14 is a chart plotting admittance versus frequency for the radially poled BB hydrophone at different steps of fabrication embodying the invention.

The entire device was then dip-coated with a ~100 μm thick insulating polyurethane polymer (Hysol US0028 from Dexter Electronic Materials Division). Admittance vs. frequency response of the electroactive ceramic transducers measured at different steps of the fabrication process are shown in FIG. 14.

Underwater hydrophone performance tests of electroactive hollow sphere transducers were carried out at the Applied Research Laboratory at Penn State University. The anechoic tank test facility consists of a water tank with 5.5 m in depth, 5.3 m in width and 7.9 m in length. A pure tone sinusoidal pulse signal of 2 msec duration is applied to the test transducer and its acoustic output is monitored with a standard F33 hydrophone. The test transducer and the standard are positioned at a depth of 2.74 m and separated by a distance of 3.16 m. Parameters measured for the hollow sphere hydrophones are Free-Field Voltage Sensitivity (FFVS), transmit voltage response (TVR) and acoustic beam patterns. The underwater test results presented in this example are obtained from the new design shown in FIG. 3.

Since a hydrophone translates an acoustic signal into a potential difference, the sensitivity of a hydrophone is usually expressed in terms of decibels relative to one volt generated when the hydrophone is exposed to an acoustic pressure of 1 μPa. Sensitivity measurements are generally taken along the axis in which maximum sensitivity is obtained (acoustic axis). However, in our case, the BB hydrophones are expected to display an omnidirectional response. Therefore, the axis of structural symmetry, i.e., the 'Z' axis indicated in FIG. 3, is taken as the principal acoustic axis to which directional characteristics are referred.

Figure 15:
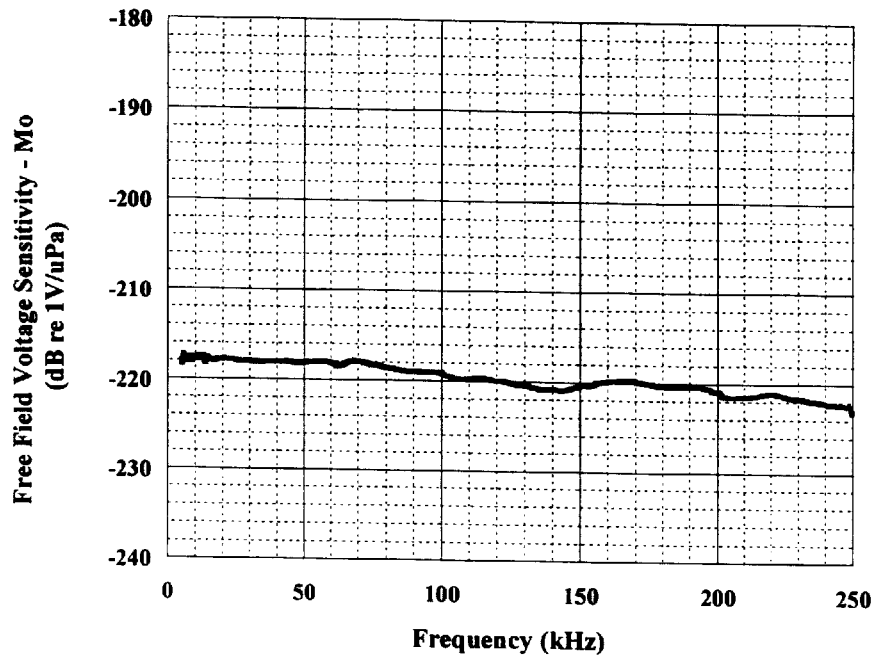
FIG. 15 is a chart plotting the free field voltage sensitivity versus frequency for the radially poled BB hydrophone embodying the invention.
Figure 16:
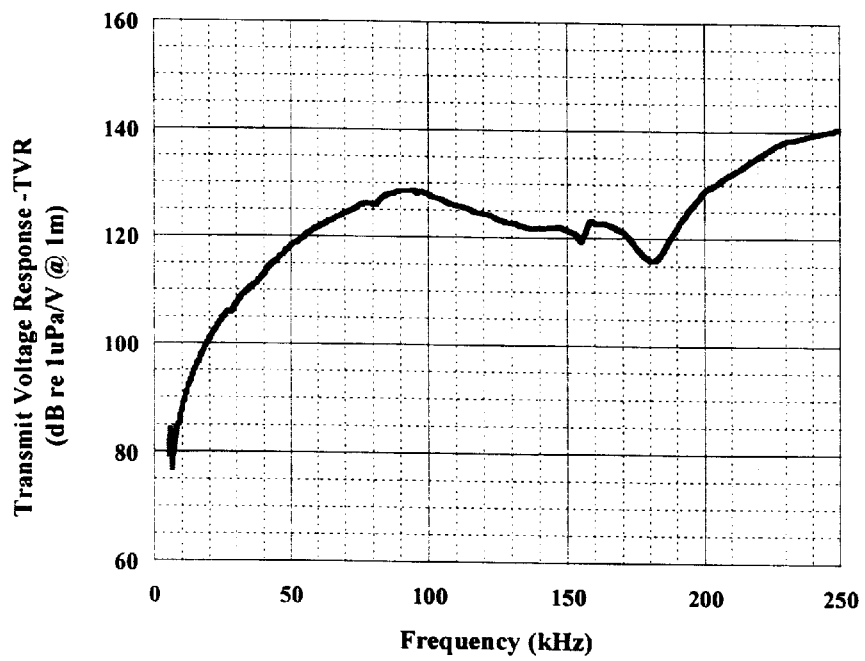
FIG. 16 is a chart plotting the transmit voltage response versus frequency for the radially poled BB hydrophone embodying the invention.

The free field voltage sensitivity of a hollow sphere with approximately a 1.33 mm radius and ~75 μm wall thickness is shown in FIG. 15. Results indicate an approximate sensitivity of −215 dB re 1V/μPa with a fairly flat response in a very broad frequency range from 5 kHz up to 250 kHz. Although, the sensitivity is not very high in numerical value, the fact that the sensitivity of the hydrophone stays flat in a broad frequency range makes this device attractive as a broadband receiver. In addition to the sensitivity measurements, Transmit Voltage Response (TVR) of the BB hollow spheres have also been measured in order to evaluate their performance as underwater projectors. The TVR response is shown in FIG. 16. Results indicate a reasonable TVR above 50 kHz, and an increasing trend above 180 kHz.

Figure 17:
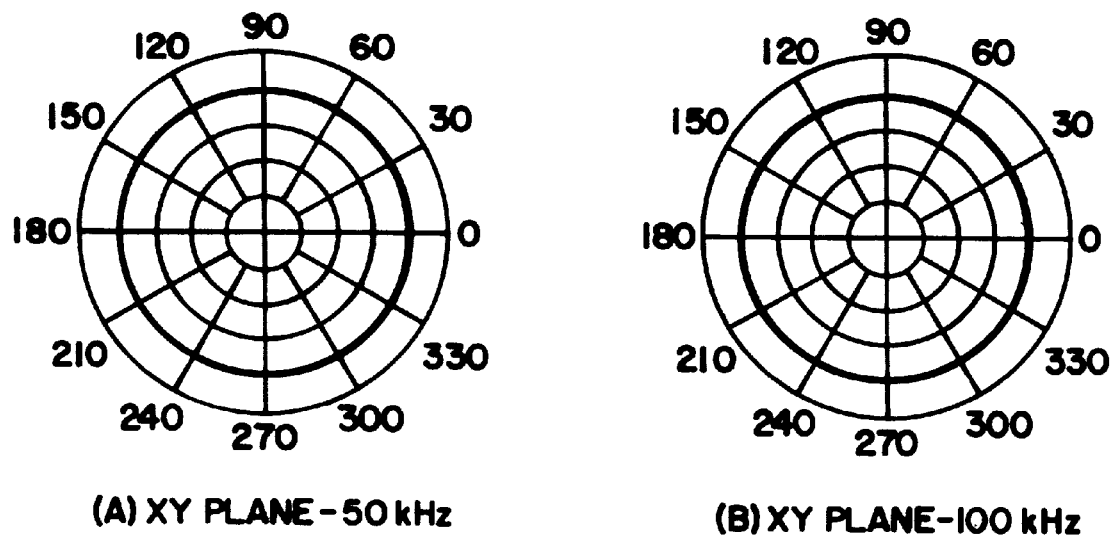
FIG. 17 illustrates polar charts plotting the directivity beam patterns in X-Y plane at two frequencies for the radially poled BB hydrophone embodying the invention.

Sensitivity of the BB hydrophones is also examined in different directions to evaluate the directional characteristics of the devices. These measurements are taken in the X-Y plane, i.e. parallel to the equatorial plane of the sphere. Directivity beam patterns for the X-Y plane are shown in FIG. 17 for two frequencies. As it is clear from the directivity measurements BB hydrophones display omnidirectional receive characteristics from 5 kHz up to 100 kHz in three-dimensional space.

EXAMPLE 2

Following the sintering step, spheres are encased in Crystal Bond™. Then the encased spheres are drilled from the top with a 800 μm diamond coated drill bit. After opening the first access hole, the spheres are then removed from Crystal Bond™, and encased again, this time the first hole located at the bottom. A second access hole is drilled sharing the same axis with the first one. Following the drilling process, spheres are removed from the Crystal Bond™ and cleaned with acetone and dried in oven at 150° C. Application of electrode layers on the sphere surfaces is carried out in two different ways to accommodate two different poling configurations.

In the first poling configuration, the inner surfaces of the spheres are first coated with an air-dry silver (Conductive Silver 200, Demetron GmbH) electrode. After a thin outer circumferential region of the spheres is masked, the outer surface of the spheres is again coated with sputtered gold electrode. Spheres are then fixed on the metal needle core by attaching the inner electrode to the needle and connecting the outer electrode to a silver wire using silver epoxy adhesive. These samples are then poled radially in a silicone oil bath at 120° C. by applying an electric field of 50 kV/cm. A schematic drawing of the radially-poled samples is shown in FIG. 4.

In the second poling configuration, spheres are fixed on a metal needle core coated with an insulator. Both holes are tapped and sealed using a conductive silver epoxy adhesive (E-solder #3021, Insulating Materials, Inc.). This is followed by coating a thick equatorial region of the spheres with a masking tape and sputtering the samples with gold electrode material. Since the region underneath the masking tape is not coated, it will be the actively poled and driven portion of the sphere. After connecting one electrode to the metal needle and the other electrode to a silver lead wire of 20 μm diameter using silver epoxy adhesive, samples are poled tangentially in a silicone oil bath at 120° C. by applying an electric field of 50 kV/cm. A schematic drawing of the tangentially-poled samples is shown in FIG. 5.

Figure 18:
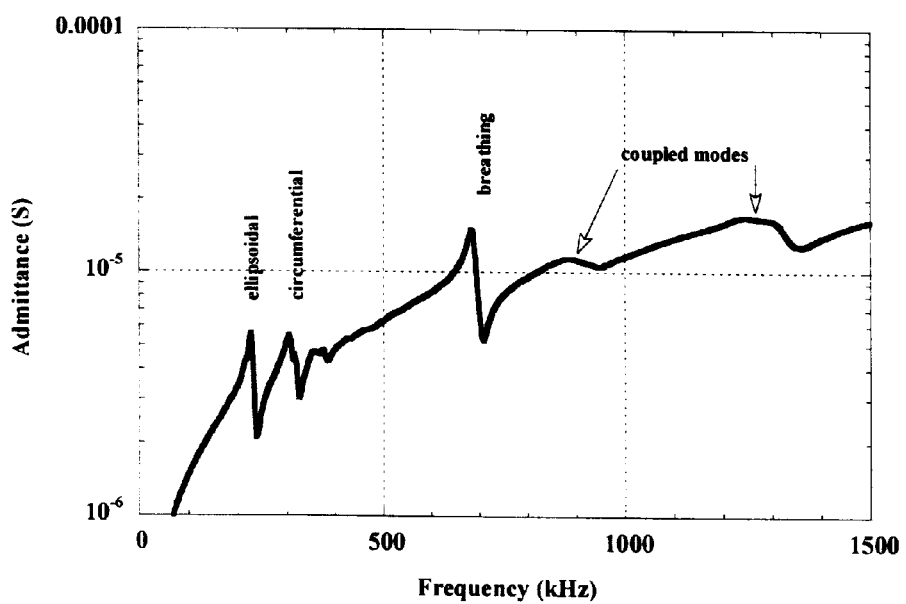
FIG. 18 illustrates a chart plotting admittance versus frequency for the tangentially poled BB transducer embodying the invention.

Transducer characteristics and the performance of the machined and poled electroactive ceramics are evaluated by dielectric measurements using an HP Multifrequency LCR meter at 1.0 volt and 1.0 kHz, and by admittance measurements using a HP Impedance-Gain Phase Analyzer up to 100 MHz in frequency. Based on the results of these measurements, tangentially-poled BB transducers have a capacitance of 3–5 pF. Admittance vs. frequency measurements, given in FIG. 18 indicate that spheres with this configuration have 3 main modes of vibration: an ellipsoidal distortion mode at ~450 kHz, a higher order circumferential mode at ~750 kHz and a breathing mode at ~1.25 MHz. Coupled modes at higher frequencies are also observed. However, these frequencies should not be taken as absolute values because the dimensions of the sphere as well as the size of the electrode gap affect the resonance frequencies. Dielectric measurements taken from the radially poled quasi-omnidirectional spheres indicate a higher capacitance of 150–250 pF.

Again, capacitance of a sphere transducer depends on the wall thickness and the size of the electrode area and the values given in this example should not be taken as absolute values. Admittance vs. frequency measurements indicate the presence of a distorted breathing mode vibration near 1 MHz, and a thickness mode vibration at frequencies above 10 MHz.

EXAMPLE 3

Following the sintering step, spheres are encased in Crystal Bond™. Then the encased spheres are ground down to a spherical shell of 1–2 mm in diameter using a polishing table. After removing these spherical shells from the Crystal Bond™ using acetone as the solvent, samples are dried in oven at 150° C. Both surfaces of the samples are then coated with gold electrode material by sputtering. Radial poling of the samples is performed in a silicone oil bath at 120° C. by applying an electric field of 80 kV/cm. After poling, a conductive backing of highly attenuative silver-loaded epoxy (Ablebond 16-1 LV, Ablestik Lab., Rancho Dominguez, Calif.) is centrifuged onto the convex surface.

A high speed lathe is used to turn the rear surface of the element back to prevent contact with the ground electrode and a true circle is formed. The self-focused elements are then mounted in a SMA connector for testing using Lockwood's method and coated with Parylene®. A schematic drawing of the finished transducer is shown in FIG. 6.

Results of the impedance vs. frequency measurements indicate that the spherically focused BB transducers have two main modes of vibration for the radial poling configuration: (1) a radial mode around 1 MHz utilizing the $d_{31}$ coefficient in which the spherical shell vibrates similar to a disk, and (2) a wall thickness mode beyond 10 MHz utilizing the $d_{33}$ coefficient (See Alkoy et al., "Focussed Spherical Transducers for Ultrasonic Imaging", Proc. Of the IEEE, Int'l Ultrasonics Symposium, pp991–996, 1997). The frequency range of these vibrations can be shifted to higher or lower frequencies by changing the sphere size, shell diameter or wall thickness of the spheres. Specifically, increasing the initial sphere size will cause a corresponding shift in the radial mode resonance frequency towards lower frequencies, and an increase in the wall thickness of the sphere will result in a transducer with a thickness mode resonance frequency shifted towards lower frequencies. Sample results obtained from characterization of focused BB transducers are presented in Table 1. The following results and numerical values are given merely as examples and do not impose limitations on this embodiment of the invention.

TABLE 1

Selected properties of focused spherical transducers

| Material | Wall Thickness (µm) | Capacitance (pF) | Resonance Frequencies (MHz) | |
|---|---|---|---|---|
| | | | Radial Mode | Thickness Mode |
| PZT-4 | 170–260 | 135 | 1.263 | 8.245 |
| PZT-5A | 89 | 325 | 1.396 | 32.150 |
| PZT-5A | 51 | 410 | 1.391 | 40.375 |

Figure 19:
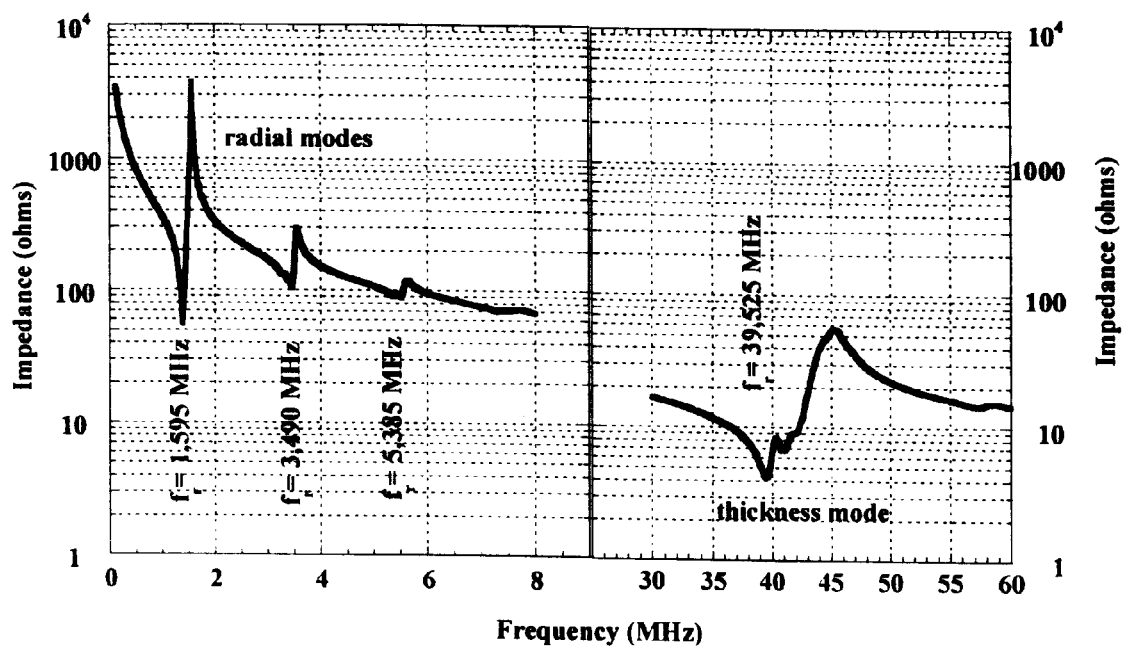
FIG. 19 illustrates a chart plotting impedance versus frequency for a focused BB transducer embodying the invention.

An experimental impedance-frequency spectrum is shown in FIG. 19 for a focused sphere transducer with a wall thickness of 63 µm. Measurement is taken in-air from a free sphere with no backing. From the measurements the thickness mode electromechanical coupling coefficient, $k_t$ was calculated to be 0.51. Application of backing was found to shift the thickness mode resonance frequency towards higher frequency range.

Transducers were also tested in a water bath by using them both as transmitters and receivers. Excitation was achieved using a Panametrics model 5900 PR computer controlled pulser receiver. Due to the thin composite structure, 6 dB of attenuation is included in the line before the transducer to protect against breakdown of the transducer element. The transducer was excited with a 16 V monocycle pulse, and the pulse echo response was obtained by recording reflections from a smooth metal target placed at the transducer's focal point. The focal distance was set by adjusting the transducer-reflector separation until a maximum amplitude of returned signal was obtained.

The reflected waveform is received at 50 ohms and digitized on a 500 MHz Lecroy oscilloscope. A limiter/expander setup is used to account for the transmission line effects seen in the coaxial cable at these elevated frequencies. The waveform is then downloaded to a PC via GPIB for later processing. Bandwidth and insertion loss measurements are made from frequency domain data calculated from the downloaded time domain data using the MathCad software package.

Figure 20:
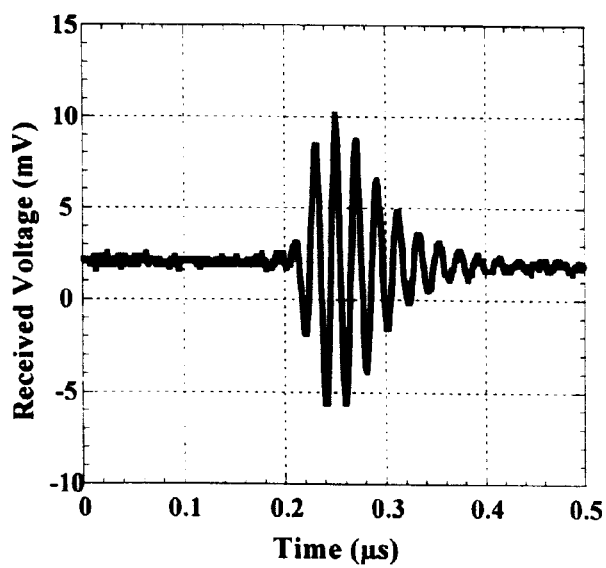
FIG. 20 illustrates a chart plotting received voltage versus time for focused BB transducer embodying the invention.
Figure 21:
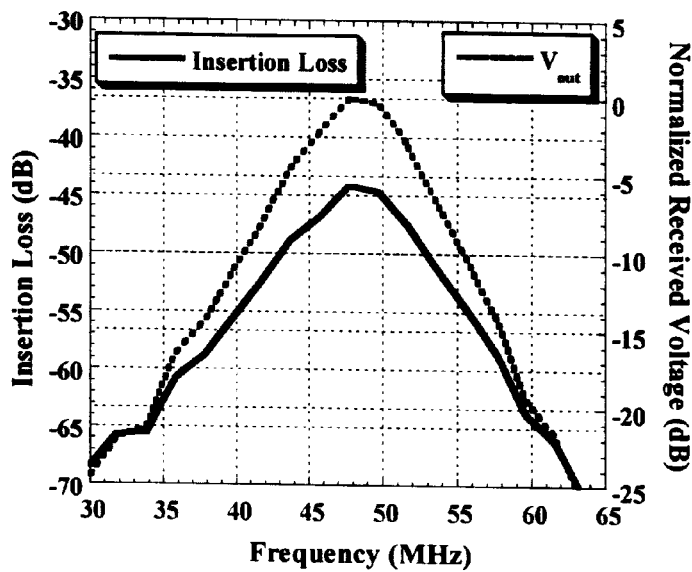
FIG. 21 illustrates a chart plotting insertion loss and normalized received voltage versus frequency for focused BB transducer embodying the invention.

The pulse echo response of the transducer is given in FIG. 20. Bandwidth and insertion loss of the transducer is calculated from frequency domain data using MathCad from the measured time domain data. The results of these calculations are plotted in FIG. 21. The pulse is centered at 47.7 MHz with a 6 dB bandwidth of 22%. A minimum insertion loss of −44 dB was obtained from the samples. At this preliminary stage, the bandwidth of the focused BBs is low and insertion loss is high compared to commercially available transducers. However, improvements are possible through decreasing size of the shells and designing proper backing and quarter wave matching layers. According to Zipparo et al., single element high frequency transducers made from PZT materials with areas larger than 1 mm$^2$ have an electrical impedance substantially lower than the 50 Ω normally used in electronic operations. This results in higher insertion losses and longer pulse length. This problem can be alleviated by either using a piezoelectric material with a lower dielectric constant, or by decreasing the area of the element resulting in lower capacitance and higher impedance, or by using a tuning circuit for electrical impedance matching.

EXAMPLE 4

In the preliminary studies of array fabrication, electroactive ceramic hollow spheres (spheres with piezoelectric PZT-5A composition are presented in this example) are coated with conductive electrodes and are poled radially, or tangentially, similar to their single element full sphere counterparts. Sputtered gold is used as the outer electrode for both of the poling configurations, whereas an air-dry silver paint is used as inner electrode in the radially poled BBs. Four of these elements are then mounted on a stiff polymer substrate in an orderly fashion to form a 2×2 array using epoxy resin. Via holes are drilled on the stiff polymer substrate prior to mounting the spheres in order to allow the wire connections to pass through. Spheres in these arrays are then connected electrically in parallel. These arrays of spheres are then coated with a thin layer of polyurethane.

Figure 7:
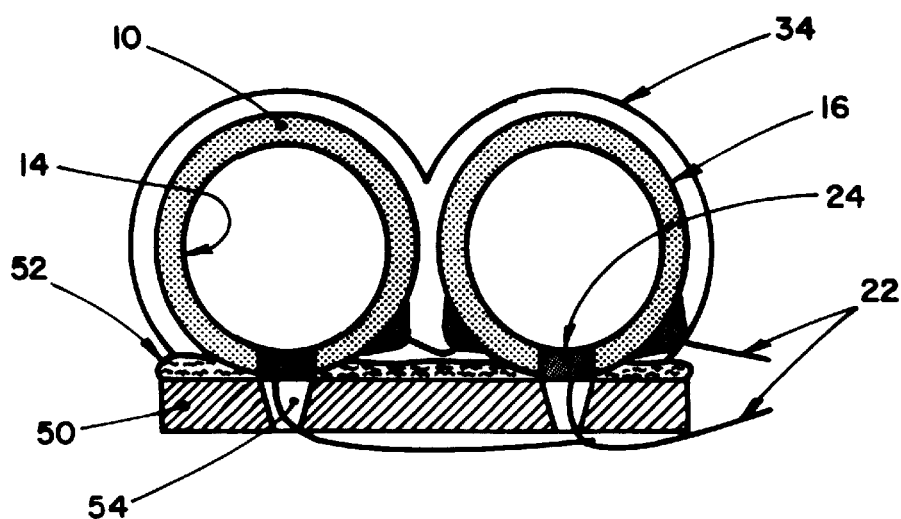
FIG. 7 is a side sectional view of an array of radially poled electroactive ceramic hollow spheres connected in parallel embodying the invention.
Figure 8:
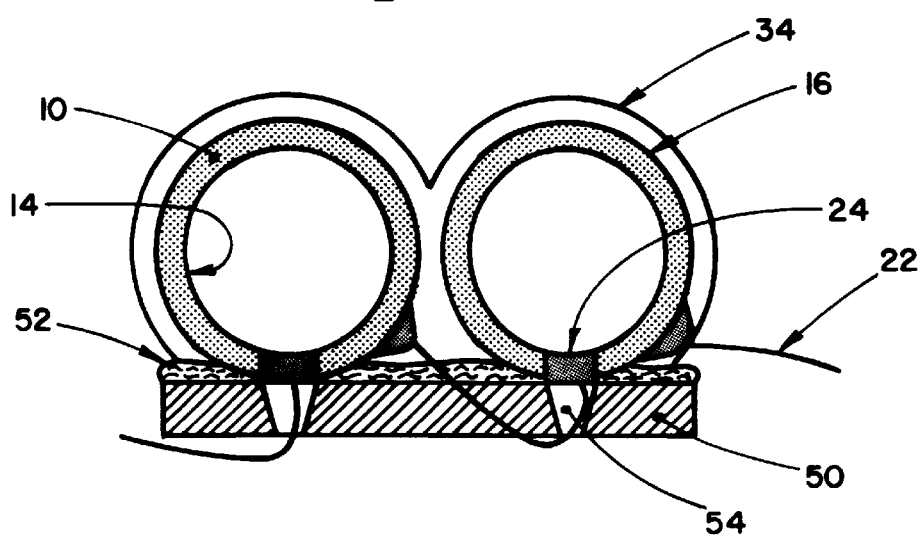
FIG. 8 is a side sectional view of an array of radially poled electroactive ceramic hollow spheres connected in series embodying the invention.
Figure 9:
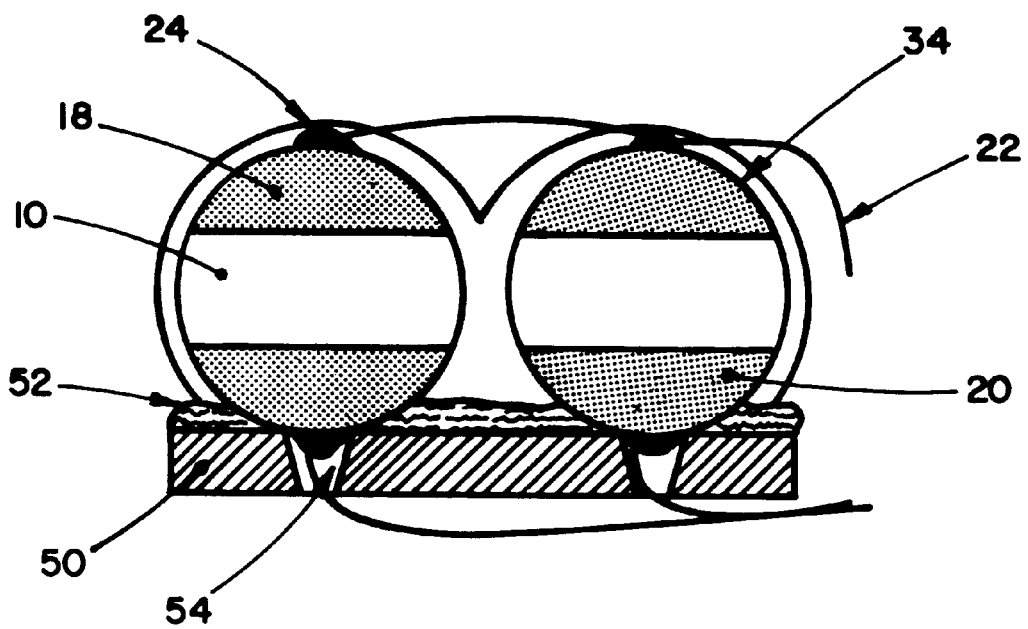
FIG. 9 is a side sectional view of an array of tangentially poled electroactive ceramic hollow spheres connected in parallel embodying the invention.
Figure 10:
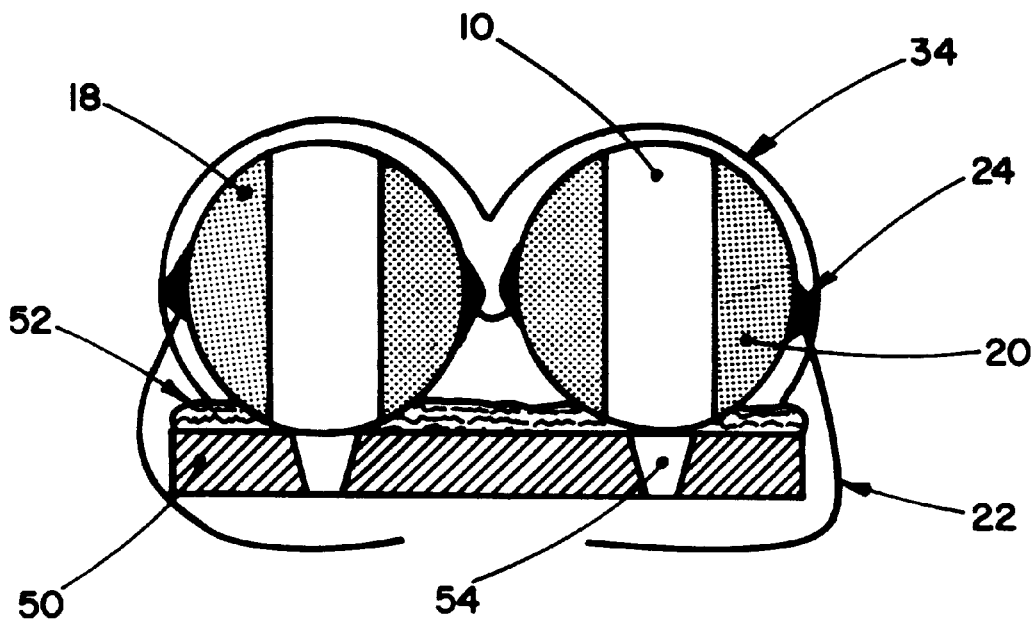
FIG. 10 is a side sectional view of an array of tangentially poled electroactive ceramic hollow spheres connected in series embodying the invention.

Schematic drawings of the BB transducer array designs that are discussed in this example are given in FIG. 7 for a 2×2 array of radially poled BB transducers connected in parallel and in FIG. 9 for a 2×2 array of tangentially poled BB transducers connected in parallel.

Dielectric characterization of the arrays of BBs indicates that capacitance of the arrays followed the expected trend of series and parallel capacitor relations. Measured capacitance values of arrays of radially poled BBs are found to range from 100 pF up to 3,000 pF. Tangentially poled sphere arrays yield very low (15–20 pF) capacitance values, similar to their single element counterparts. In the admittance vs. frequency spectrum of the arrays resonance frequencies are observed around the characteristic resonance of the constituent elements. However, they are found to be damped due to the stiff bonding between the sphere and the substrate, as well as due to the thick, stiff inner electrode in the case of radially-poled spheres.

Figure 22:
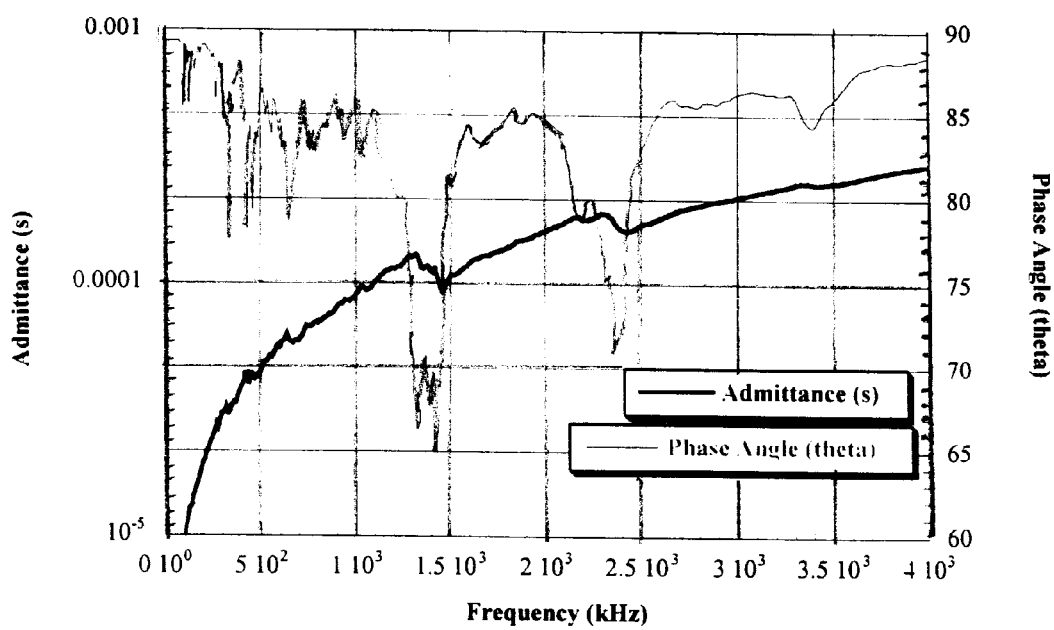
FIG. 22 illustrates a chart plotting admittance and phase angle versus frequency for an array of tangentially poled electroactive ceramic hollow spheres connected in series embodying the invention.

FIG. 22 shows the admittance vs. frequency response of a 4-elements array prepared from tangentially-poled spheres connected in parallel.

As part of the transducer characterization the hydrostatic piezoelectric charge coefficient ($d_h$) of the transducer are measured and the hydrostatic piezoelectric voltage coefficient ($g_h$) was calculated. The $d_h$ coefficient determines the charge delivered by the hydrophone to the preamplifier, and the $g_h$ coefficient determines the open-circuit voltage of the transducer. The $(d_h \times g_h)$ product can be taken as a measure of the signal-to-noise ratio (SNR) obtainable from a unit volume of piezoelectric material under conditions where the dominant noise source is the preamplifier. Therefore, these two values $(d_h \times g_h)$ were calculated as an acceptable figure of merit for a volume expander hydrophone.

Figure 23:
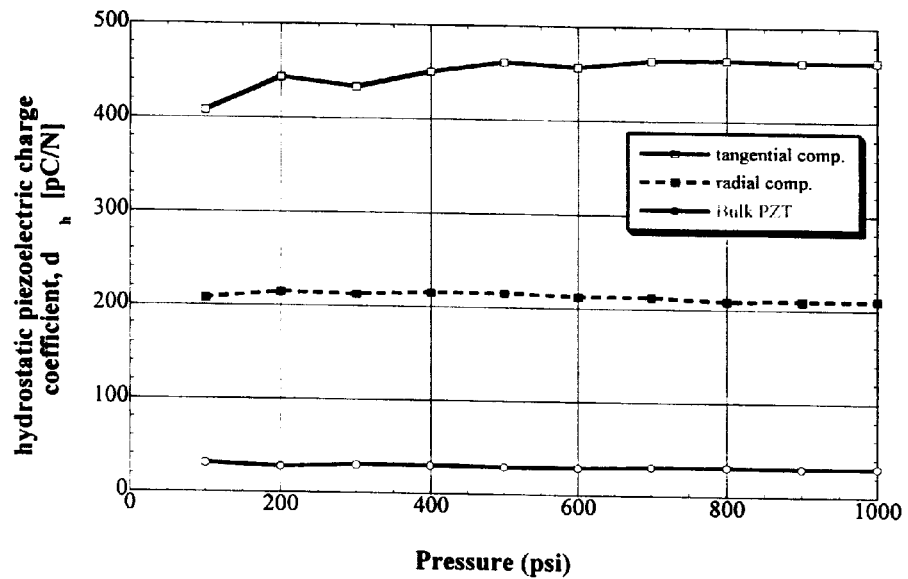
FIG. 23 illustrates a chart plotting hydrostatic piezoelectric charge coefficient ($d_H$) versus hydrostatic pressure for arrays of tangentially poled electroactive ceramic hollow spheres connected in parallel, radially poled electroactive ceramic hollow spheres connected in parallel and for bulk PZT
Figure 24:
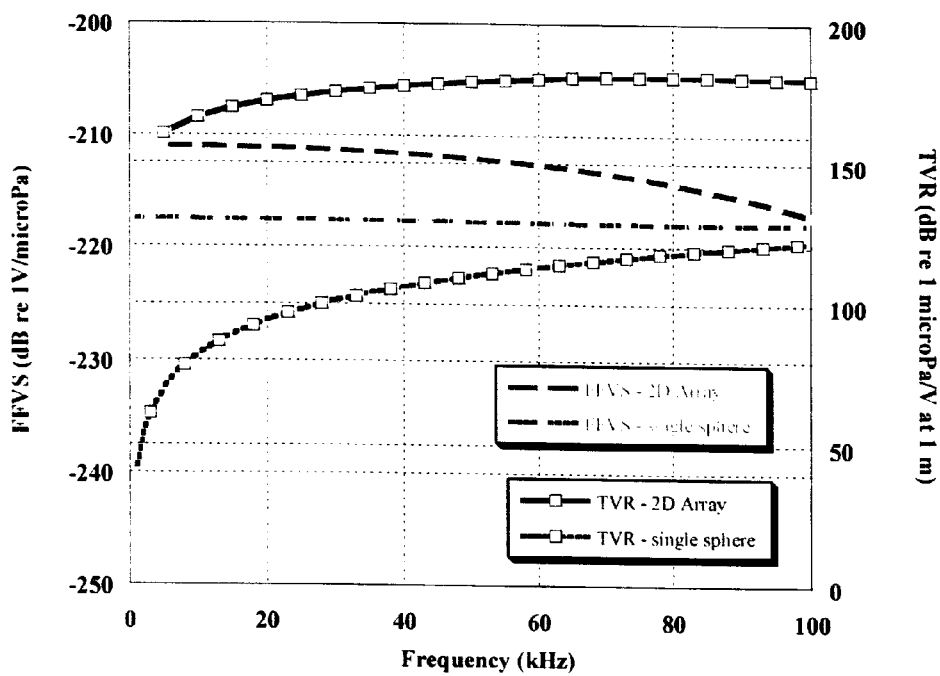
FIG. 24 illustrates a chart plotting the free field voltage sensitivity versus frequency, and transmit voltage response versus frequency for single BB transducers and for two dimensional arrays of BB transducers obtained from finite element analysis.

A comparison of the $d_h$ of a tangentially poled array, a radially poled array, and that of a bulk PZT disk is shown in FIG. 23. As it is seen from this plot, arrays of spheres have a much higher hydrophone figure of merit compared to that of bulk PZT. Additionally, computations of Transmit Voltage Response (TVR) and Free Field Voltage Sensitivity (FFVS) using Finite Element Analysis (FEA) Methods shows that 2 dimensional arrays consisting of more than 9 radially poled spheres display superior properties compared to a single electroactive hollow ceramic sphere. A comparison of he underwater transducer performance of radially poled ingle element and 2D array of spheres obtained from finite element analysis is shown in FIG. 24.

This invention demonstrates that transducers fabricated from electroactive ceramic hollow spheres are capable of solving some of the technical problems currently faced in ultrasonic guidance systems, biomedical ultrasound imaging systems, and underwater hydrophone applications. In addition, the low cost and mass production of these transducers allows the use of one-time, throw-away transducers.

While we have illustrated and described the preferred embodiments of our invention. The specific examples presented in this disclosure are not to be interpreted as limiting, but merely as a support for the invention as claimed and as appropriate representation for the teaching one skilled in the art to variously employ the present invention in any appropriate embodiment. Various alternatives and modifications can be devised by those skilled in the art without departing from the invention. We therefore desire and intend to embrace all such alternatives, modifications and variances which fall within the scope of the present invention and its resulting claims.

We claim:

1. An electroactive device comprising:

an electroactive ceramic hollow sphere having an inner surface, an outer surface, a wall thickness aspect and a radius aspect;

a first access hole through said sphere;

a second access hole through to the opposite side of said sphere;

an interior passageway to enable an instrumentality to pass through said first and second access holes and said sphere;

conductive electrodes on said sphere; and conductor means for applying an electrical potential between said conductive electrodes to enable a field to be applied to said sphere that causes a dimension change in the radius aspect and thickness aspect thereof.

2. The device as recited in claim 1, wherein said electroactive ceramic hollow sphere has a $d_{33}$ direction parallel to said thickness aspect, and $d_{31}$ & $d_{32}$ directions parallel to said sphere surfaces.

3. The device as recited in claim 2, wherein said radius aspect has a dimension of about 0.1 to 5 millimeters and a wall thickness aspect has a dimension of about of about 1 to 1000 micrometers.

4. The device of claim 2, further comprising:

an instrumentality from the group consisting of a rod, a hollow cylinder, and a catheter, positioned in both said first and second access holes to both provide physical support for said sphere and also to support said conductor means.

5. An electroactive device comprising:

an electroactive ceramic hollow sphere having an inner surface, an outer surface, a wall thickness aspect and a radius aspect;

a first access hole through said sphere;

a second access hole through said sphere, conductive electrodes on opposed inner and outer surfaces of said sphere;

conductor means for applying an electrical potential between said conductive electrodes to enable a field to be applied to said sphere that causes a dimension change in the radius aspect and thickness aspect thereof;

wherein a rod is extended through said first access hole and said second access hole and including an interior passageway to enable an instrumentality to pass through said first and second access holes and said sphere and said rod is positioned in said access holes to both provide physical support for said sphere and also to support said conductor means; and wherein said electroactive ceramic hollow sphere is polarized radially and has a $d_{33}$ direction parallel to said thickness aspect, and $d_{31}$ & $d_{32}$ directions parallel to said sphere surfaces.

6. The device as recited in claim 1, wherein said electroactive ceramic hollow sphere exhibits a piezoelectric characteristic.

7. The device as recited in claim 1, wherein said conductive electrodes are on opposed surfaces, wherein said opposed surfaces are an inner surface and an outer surface of said sphere.

8. The device as recited in claim 1, wherein said conductive electrodes are both positioned on said outer surface of said sphere, one conductive electrode positioned about said first access hole and a second conductive electrode positioned about said second access hole; and wherein said electroactive ceramic hollow sphere has a $d_{33}$ direction perpendicular to said thickness aspect, and $d_{31}$ direction parallel & $d_{32}$ direction perpendicular to said sphere surfaces, respectively.

9. The device as recited in claim 8, wherein said radius aspect has a dimension of about 0.1 to 5 millimeters and a wall thickness aspect has a dimension of about of about 1 to 1000 micrometers.

10. The device of claim 8, further comprising: an instrumentality from the group consisting of a rod, a hollow cylinder, and a catheter, positioned in both said first and second access holes to both provide physical support for said sphere and also to support said conductor means.

11. An electroactive device comprising:

an electroactive ceramic hollow sphere having an inner surface, an outer surface, a wall thickness aspect and a radius aspect;

a first access hole through said sphere;

a second access hole through said sphere, conductive electrodes disposed on the outer surface of said sphere;

conductor means for applying an electrical potential between said conductive electrodes to enable a field to be applied to said sphere that causes a dimension change in the radius aspect and thickness aspect thereof;

wherein a rod is extended through said first access hole and said second access hole and including an interior passageway to enable an instrumentality to pass through said first and second access holes and said sphere; and wherein said electroactive ceramic hollow sphere has a $d_{33}$ direction perpendicular to said thickness aspect, and $d_{31}$ direction parallel & $d_{32}$ direction perpendicular to said sphere surfaces.

12. The device as recited in claim 11, wherein said conductive electrodes are both positioned on said outer surface of said sphere, one conductive electrode positioned about said first access hole and a second conductive electrode positioned about said second access hole.

13. The device as recited in claim 8, wherein said electroactive ceramic hollow sphere exhibits a piezoelectric characteristic.

14. An electroactive device comprising:

an electroactive ceramic comprising a concave-shaped shell having a substantially hemispherical shape or less than hemispherical shape, but truncated by a chord that does not pass through a center of radius of said hemispherical shape, said shell having a radius aspect of 0.1 to 5 millimeters and a wall thickness aspect of 1 to 1000 micrometers, and a $d_{33}$ direction parallel to said thickness aspect, and $d_{31}$ & $d_{32}$ directions parallel to said surfaces of said sphere;

conductive electrodes on opposed surfaces of the said electroactive ceramic shell;

conductor means for applying an electrical potential between said conductive electrodes to enable a field in the $d_{33}$ direction that causes a dimension change in the radius and thickness of said shell.

15. The device of claim 14, wherein said electroactive ceramic shell is poled radially along the $d_{33}$ direction and exhibits a piezoelectric characteristic.

16. The device of claim 14, wherein said electrical potential causes said shell to create a focused acoustic beam with a focal length equal to the radius of said hemispherical shape.

17. The device of claim 14, further comprising:

a polymer-based backing material adhered to a convex surface of said electroactive ceramic shell; and a further polymer-based material positioned on a concave surface of said electroactive ceramic shell, said further polymer-based material chosen to match an acoustical impedance of the said device to a medium of use, to electrically insulate said device and to form a watertight environmental insulation layer for said device.

18. An electroactive device comprising:

an array of a plurality of electroactive ceramic hollow spheres constructed in accord with claim 8, and wherein said conductor means for each sphere are energized to cause said array to exhibit a determined beam characteristic.

19. An electroactive device comprising:

an array of a plurality of thin-wall electroactive ceramic hollow spheres constructed in accord with claim 2 and wherein said conductor means for each sphere are energized to cause said array to exhibit a determined beam characteristic.

20. An electroactive device comprising:

an array of a plurality of thin-wall electroactive ceramic shells constructed in accord with claim 14 and wherein said conductor means for each said shell is energized to cause said array to exhibit a determined beam characteristic.

21. An electroactive device comprising:

an array of a plurality of electroactive ceramic hollow spheres of radius aspect of 0.1 to 5 millimeters and a wall thickness aspect of 1 to 1000 micrometers;

a matrix material in which said electroactive ceramic hollow spheres are embedded, said matrix forming two parallel surfaces and poled through a thickness aspect thereof;

conductive electrodes positioned on said parallel surfaces; and conductor means for applying an electrical potential across said conductive electrodes to enable a field that causes a dimension change in the radius and thickness of said electroactive ceramic hollow sphere.

22. The device of claim 21, wherein said electroactive ceramic hollow spheres are embedded in the matrix so that opposite poles thereof are partially exposed through the parallel surfaces, respectively, and said electrodes are in physical contact with said exposed surfaces of said spheres.

23. The device of claim 22, wherein said electroactive ceramic hollow spheres are embedded in the matrix so that opposite poles thereof are partially exposed through the parallel surfaces, enabling interiors of said spheres to be accessed via holes in said areas that are partially exposed, said hollow spheres being filled with a further matrix material.

24. The device of claim 22, wherein said electroactive ceramic hollow spheres are embedded in the matrix so that opposite poles thereof are partially exposed through the parallel surfaces, with at least portions of the exposed spheres being removed to expose interiors of said spheres, and further comprising caps positioned on said exposed portions of said spheres.

25. The device of claim 24, wherein said caps are conductive.

26. The device of claim 24, wherein said caps are nonconductive.

* * * * *